(12) United States Patent
Ben-Hur (10) Patent No.: US 9,474,844 B1
(45) Date of Patent: Oct. 25, 2016

(54) METHODS FOR PATHOGEN INACTIVATION IN BLOOD USING UV IRRADIATION WHILE MINIMIZING HEAT TRANSFER THERETO

(71) Applicant: Ehud Ben-Hur, Loveland, CO (US)

(72) Inventor: Ehud Ben-Hur, Loveland, CO (US)

(73) Assignee: Hemalux LLC, Mahwah, NJ (US)

( * ) Notice: Subject to any disclaimer, the term of this patent is extended or adjusted under 35 U.S.C. 154(b) by 0 days.

(21) Appl. No.: 14/982,861

(22) Filed: Dec. 29, 2015

Related U.S. Application Data (62) Division of application No. 14/521,398, filed on Oct. 22, 2014, now Pat. No. 9,265,876.

(51) Int. Cl.
   *A61L 2/00* (2006.01)
   *A61M 1/36* (2006.01)
   *A61L 2/10* (2006.01)
   *A61K 41/00* (2006.01)

(52) U.S. Cl.
   CPC ........... *A61M 1/3681* (2013.01); *A61L 2/0047* (2013.01); *A61K 41/0019* (2013.01); *A61L 2/10* (2013.01); *A61M 2202/0413* (2013.01)

(58) Field of Classification Search
   CPC .... A61L 2/0047; A61L 2/10; A61M 1/3681; A61K 41/0019
   See application file for complete search history.

(56) References Cited

U.S. PATENT DOCUMENTS

| | | | | |
|---|---|---|---|---|
| 2,588,223 A * | 3/1952 | Stamm | A61L 2/10 | 422/24 |
| 4,101,424 A * | 7/1978 | Schooley | B41F 23/0409 | 250/492.1 |
| 4,683,889 A * | 8/1987 | Edelson | A61M 1/3686 | 600/3 |
| 5,133,932 A * | 7/1992 | Gunn | A61L 2/10 | 210/243 |
| 5,184,020 A * | 2/1993 | Hearst | B01J 19/123 | 250/454.11 |
| 5,304,113 A * | 4/1994 | Sieber | A61K 31/505 | 604/20 |
| 5,503,721 A * | 4/1996 | Hearst | B01J 19/123 | 204/157.15 |
| 6,054,097 A * | 4/2000 | Mass | A61L 2/08 | 210/748.11 |
| 6,113,566 A * | 9/2000 | Schleicher | A61M 1/3681 | 604/6.08 |
| 6,464,936 B1 * | 10/2002 | Mowat | A61L 2/0011 | 250/438 |
| 6,586,172 B1 * | 7/2003 | Gunn | A61L 2/0011 | 356/426 |
| 7,118,852 B2 * | 10/2006 | Purdum | C12N 13/00 | 435/173.1 |
| 7,993,580 B2 * | 8/2011 | Anderle | A23L 3/26 | 250/435 |
| 8,377,375 B2 * | 2/2013 | Anderle | A23L 3/26 | 250/435 |
| 2003/0049809 A1 * | 3/2003 | Kaiser | A23L 3/28 | 435/173.1 |
| 2006/0217651 A1 * | 9/2006 | Hutchinson | A61M 1/3681 | 604/6.01 |
| 2006/0270017 A1 * | 11/2006 | Reiter | C12N 7/00 | 435/235.1 |
| 2006/0270960 A1 * | 11/2006 | Karp | A61M 1/3681 | 604/6.08 |
| 2009/0156976 A1 * | 6/2009 | Korbling | A61M 1/3681 | 604/5.02 |
| 2010/0189597 A1 * | 7/2010 | Hlavinka | A61M 1/0209 | 422/22 |
| 2011/0206554 A1 * | 8/2011 | Anderle | A23L 3/26 | 422/3 |
| 2013/0119265 A1 * | 5/2013 | Anderle | A23L 3/26 | 250/432 R |
| 2014/0251925 A1 * | 9/2014 | Petrie | A61M 1/3681 | 210/748.11 |
| 2014/0341777 A1 * | 11/2014 | Deshays | A61L 2/24 | 422/24 |
| 2015/0231287 A1 * | 8/2015 | Lin | A61L 2/10 | 607/80 |

\* cited by examiner

*Primary Examiner* — Wyatt Stoffa
(74) *Attorney, Agent, or Firm* — Boris Leschinsky (57) ABSTRACT

Methods for pathogen reduction in donor blood are performed by exposure of blood to UVC irradiation. Unwanted wavelengths of light, mostly in the infrared spectra, may be precluded from reaching blood by providing a layer of IR-absorbing fluid positioned between blood and the source of UV irradiation, whereby minimizing energy absorption and heating of blood. Some embodiments further disclose utilizing the same IR-absorbing fluid to actively cool blood by flowing the IR-absorbing fluid along the blood flow path.

6 Claims, 10 Drawing Sheets

METHODS FOR PATHOGEN INACTIVATION IN BLOOD USING UV IRRADIATION WHILE MINIMIZING HEAT TRANSFER THERETO

CROSS-REFERENCE DATA

This patent application is a divisional application in the case of my co-pending U.S. patent application Ser. No. 14/521,398 filed 22 Oct. 2014 with the same title. This patent application claims a priority date benefit from the '398 application which is incorporated herewith in its entirety by reference.

BACKGROUND OF THE INVENTION

The present relates to systems and methods for the UV-irradiation of a biological fluid for the purposes of reduction of pathogens therein. While the primary object of the invention is to treat blood, blood-based products and synthetic blood substitutes, the concepts of the present invention may be used for treating other fluids such as those encountered in beverage industries including dairy, distilling and brewing, as well as in water treatment industries including sewerage and purification systems. Other uses of the invention contemplate treating blood from a subject and returning the blood to the subject after completion of the treatment.

The term "pathogens" is used broadly for the purposes of the present invention to include a variety of harmful microorganisms such as bacteria, fungi, viruses (including among others a human immunodeficiency virus, a hepatitis A, B and C virus, an influenza virus, a hemorrhagic fever virus such as Ebola virus etc.), parasites, molds, yeasts and other similar organisms which may be found in human or non-human blood and products derived from blood, as well as various other body fluids such (as for example milk) and synthetic fluids manufactured for use as replacements for any such body fluids or components thereof.

Blood transfusion in developed countries is very safe with regard to avoidance of transmitting of an infectious disease. This is primarily achieved by donor exclusion using questionnaires and screening for pathogens presence by means of serological methods and direct testing for nucleic acids. Despite these practices, there remains a risk of transmission of pathogens with the transfusion of cellular components of blood (such as red cells and platelets for example). This is at least in part because current screening tests leave a window of time after infection and before their sensitivity allows for detection of pathogens. In addition, screening does not takes place for rarely occurring pathogens or as yet unknown transmissible pathogens (Soland, E. M. et al. *J. Am. Med. Assoc.* 274: 1368-1373 (1995); Schreiber, G. B. et al. *New Engl. J. Med.* 334: 1685-1690 (1996); Valinsky, J. E. In: *Blood Safety and Surveillance*, Linden, J. V. and Bianco, C., Eds., Marcel Dekker, N Y, 2001, pp. 185-219).

The use of pathogen reduction technologies has the potential of eliminating the remaining risks of transmission of infectious disease as a result of blood transfusion. Various approaches have been used to sterilize blood components (Ben-Hur, E. and B. Horowitz *AIDS* 10: 1183-1190 (1996); Ben-Hur, E. and R. P. Goodrich, In: Photodynamic Inactivation of Microbial Pathogens, Hamblin, M. R. and J. Gori, Eds. RSC Publishing, U K, 2011, pp. 233-263). The most promising methods are photochemical ones, two of which were approved by regulatory agencies for pathogen reduction in platelet concentrates. The Intercept method employs a psoralen and UVA light (Lin, L. et al. *Transfusion* 37: 423-435 (1997)) and the Mirasol method uses riboflavin and UVA+UVB light (Goodrich, R. P. et al. *Transfusion Apheresis Sci.* 35: 5-17 (2006)).

Short wavelengths ultraviolet light (UVC, 180-290 nm) is a known sterilizing agent that targets the nucleic acids of microorganisms (Setlow, R. B. and J. K. Setlow *Proc. Natl. Acad. USA* 48: 1250-1253 (1962)). It has been used for pathogen reduction in optically-transparent biological fluids such as plasma (Chin, S. et al. *Blood* 86: 4331-4336 (1995)) and is being studied also in platelet concentrates (Bashir, S. et al. *Transfusion* 53: 990-1000 (2013)). However, in opaque biological fluids such as red cell concentrates as well as in whole blood, UVC penetration is very limited due to absorption of UV irradiation by the red cells. As a result, all attempts to use UV irradiation for sterilizing whole blood or red cells have been unsuccessful so far.

Therefore, there is a need for an effective system and method for reducing pathogens in a biological fluid such as blood.

Attempts to irradiate blood or other opaque biological fluids with UV light have been described before. The exposure of a biological fluid to UV irradiation can result in damage to various components of the biological fluid, for example enzymes and other functional proteins. Therefore, the UV irradiation source should not be too powerful nor may the fluid be exposed to the UV radiation for too long, if one is to avoid damaging the components of the biological fluid. On the other hand, sufficient UVC energy needs to be transmitted to the blood flow to assure substantial reduction and effective elimination of the pathogens. This balance is critical in achieving desired effectiveness of UVC treatment.

To ensure that substantially all of the fluid receives a sufficient dose of UV radiation, it has been found that intensive mixing of the fluid to be treated during UV irradiation increases the efficiency of the irradiation process. A variety of devices that include static mixers placed in the fluid flow pathway have been proposed such as those described in U.S. Pat. Nos. 6,312,593; 7,175,808; US Pat. Application Publications 2004/0039325; 2006/0270960; or PCT publications WO1997046271; WO2000020045.

In addition to mixing, a sufficient intensity of the UV irradiation needs to be provided by a source of UV irradiation. Traditional devices used as such source include low pressure and medium pressure mercury UV lamps, amalgam UV lamps, arc UV lamps, fluorescent UV lamps, halogen UV lamps, and xenon UV lamps. Such lamps have a number of disadvantages when used directly for the purposes of the present invention as they produce low level of UV output given the energy requirements, have large size, fragile and if broken represent an environmental hazard of mercury contamination. In addition, traditional UV lamps produce UV output over a broad range of UV wavelengths, some of which may be harmful to the biological fluid.

There is a need for a new exposure chamber and a new system for reducing pathogens in a biological fluid with improved source of UV irradiation and specifically with the ability to provide high intensity of UV light in a small physical size. There is also a need for a new source of UV irradiation to provide efficacious UV irradiation at desired peak wavelength with low energy consumption.

SUMMARY OF THE INVENTION

Accordingly, it is an object of the present invention to overcome these and other drawbacks of the prior art by providing a novel systems and methods for reduction of pathogens in a biological fluid by exposing the fluid to a sufficient dose of UVC irradiation but without damaging of other blood elements caused by absorption of IR spectra of wavelengths leading to excessive heating thereof.

It is a further object of the present invention to provide novel systems for reduction of pathogens in the biological fluid having sufficient UVC irradiation intensity to treat opaque biological fluids such as whole blood and blood products.

It is yet another object of the invention to provide extracorporeal systems and methods for reducing pathogen level in a blood of a subject suffering from a condition associated with a presence of blood-borne pathogens.

It is yet another object of the present invention to provide novel systems and method for treating donor blood prior to its further processing, separation into individual components and storage.

The system of the invention is designed for inactivation of pathogens in the biological fluid such as a unit of whole blood suitable for transfusion. The system includes a novel exposure chamber comprising a source of UV irradiation and a closely positioned adjacent flow path configured to expose the biological fluid to UV irradiation. The source of UV irradiation may be configured to emit ultraviolet light in the UVC range of wavelengths. In embodiments, UVC light may be used with a predetermined peak wavelength from about 250 nm to about 270 nm. The system may include a pump such as a roller pump or a centrifugal pump to propagate biological fluid such as whole blood through a UV-transparent flow path of the exposure chamber, for example in a serpentine-shaped tube. The flow path may include one or more static mixer elements to cause intermittent or continuous mixing of the biological fluid during its propagation through the flow path. The flow path may be configured for exposure of the fluid to UVC irradiation from a suitable source such as one or several UV lamps or a plurality of UV emitting diodes (UV LEDs). UV exposure of the biological fluid may be conducted at an appropriately high power density that allows sufficient UVC dose to be impinged on the fluid—such that sufficient inactivation of pathogens takes place. The treated fluid may then be propagated out of the exposure chamber and collected in a new storage bag and the disposable flow path may be discarded after use.

The novel portion of the system includes provisions for separation of the flow path from the UV irradiation source by a layer of fluid known to absorb at least some and preferably a substantial portion of infra-red radiation emanating from the source of UV irradiation, ambient light or any other light sources to which the flow path is exposed to. Such layer may be positioned between the flow path and the source of UV irradiation for the purposes of reducing or preventing heat transfer to the biological fluid from the source of UV irradiation. In other embodiments, a UV-transparent jacket surrounding the flow path is provided and the IR-absorbing fluid is circulated therethrough. Introducing the IR-absorbing fluid at a temperature lower than that of the biological fluid allows the system to both absorb the IR irradiation (to prevent it from reaching the biological fluid) as well as cool the biological fluid to counteract energy absorption resulting from exposure to UV irradiation.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF THE PREFERRED EMBODIMENT OF THE INVENTION

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

The definition of the terms "IR" or "infra-red" range of wavelengths used for the purposes of the present invention is somewhat broader than the classic definition of IR and includes a wavelength range from about 700 nm to about 1100 nm. The term "about" is used here and throughout the rest of this description to denote a deviation from the cited value by plus or minus 20 percent.

The term "UV irradiation" is used generally in this description to encompass various techniques of exposing biological fluids including blood to UV light for therapeutic purposes, such techniques are also known under other names including Ultraviolet Blood Irradiation, Photoluminescence, Ultra Violet Photoluminescence, Photo-oxidation Therapy, Ultraviolet Blood Irradiation, Hematogenous Oxygenation Therapy, and Extracorporeal Photophoresis.

Figure 1:
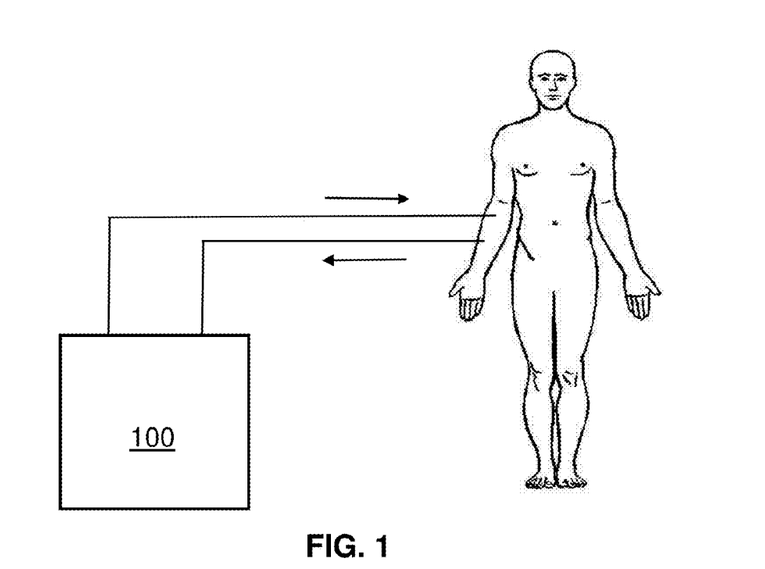
FIG. 1 is a general schematic view of the system of the invention used to treat a subject.

FIG. 1 shows a general illustration of the method and the system for treating blood. The method of the invention comprises a step of irradiating a biological fluid such as blood with UV light through a layer of IR-absorbing fluid in order to intercept IR exposure of the biological fluid and therefore prevent its unwanted heating. The method may be accomplished by using the system of the present invention for treating a subject in order to reduce his or her bloodborne pathogen count or for another useful purpose.

As mentioned above, a number of pathogens or harmful microorganisms may be susceptible to the UV irradiation (and in particular UVC irradiation) and therefore the system of the invention may be used to remove these pathogens from the blood stream. Such pathogens may include bacteria, fungi, viruses, parasites, molds, yeasts and other similar organisms. UVC light is known to disrupt the DNA or RNA of such pathogens and therefore eradicate them.

A variety of viruses may be reduced or eliminated from the blood stream or in donor blood by the present invention. Non-limiting examples of such viruses include the following: Adeno-associated virus, Aichi virus, Australian bat lyssavirus, BK polyomavirus, Banna virus, Barmah forest virus, Bunyamwera virus, Bunyavirus La Crosse, Bunyavirus snowshoe hare, Cercopithecine herpesvirus, Chandipura virus, Chikungunya virus, Cosavirus A, Cowpox virus, Coxsackievirus, Crimean-Congo hemorrhagic fever virus, Dengue virus, Dhori virus, Dugbe virus, Duvenhage virus, Eastern equine encephalitis virus, Ebola virus, Echovirus, Encephalomyocarditis virus, Epstein-Barr virus, European bat lyssavirus, GB virus C/Hepatitis G virus, Hantaan virus, Hendra virus, Hepatitis A virus, Hepatitis B virus, Hepatitis C virus, Hepatitis E virus, Hepatitis delta virus, Herpes simplex virus, Herpes zoster virus, Horsepox virus, Human adenovirus, Human astrovirus, Human coronavirus, Human cytomegalovirus, Human enterovirus 68, 70, Human herpesvirus 1, Human herpesvirus 2, Human herpesvirus 6, Human herpesvirus 7, Human herpesvirus 8, Human immunodeficiency virus, Human papillomavirus 1, Human papillomavirus 2, Human papillomavirus 16, 18, Human parainfluenza, Human parvovirus B19, Human respiratory syncytial virus, Human rhinovirus, Human SARS coronavirus, Human spumaretrovirus, Human T-lymphotropic virus, Human torovirus, Influenza A virus, Influenza B virus, Influenza C virus, Isfahan virus, JC polyomavirus, Japanese encephalitis virus, Junin arenavirus, KI Polyomavirus, Kunjin virus, Lagos bat virus, Lake Victoria marburgvirus, Langat virus, Lassa virus, Lordsdale virus, Louping ill virus, Lymphocytic choriomeningitis virus, Machupo virus, Mayaro virus, MERS coronavirus, Measles virus, Mengo encephalomyocarditis virus, Merkel cell polyomavirus, Mokola virus, Molluscum contagiosum virus, Monkeypox virus, Mononucleosis virus, Mumps virus, Murray valley encephalitis virus, New York virus, Nipah virus, Norwalk virus, O'nyong-nyong virus, On virus, Oropouche virus, Pichinde virus, Poliovirus, Punta toro phlebovirus, Puumala virus, Rabies virus, Rift valley fever virus, Rosavirus A, Ross river virus, Rotavirus A, Rotavirus B, Rotavirus C, Rubella virus, Sagiyama virus, Salivirus A, Sandfly fever sicilian virus, Sapporo virus, SARS virus, Semliki forest virus, Seoul virus, Simian foamy virus, Simian virus 5, Sindbis virus, Southampton virus, St. Louis encephalitis virus, Tick-borne powassan virus, Torque teno virus, Toscana virus, Uukuniemi virus, Vaccinia virus, Varicellazoster virus, Variola virus, Venezuelan equine encephalitis virus, Vesicular stomatitis virus, Western equine encephalitis virus, WU polyomavirus, West Nile virus, Yaba monkey tumor virus, Yaba-like disease virus, Yellow fever virus, Zika virus and synthetic viruses.

Blood borne bacteria that can be reduced or eradicated by the present invention include at least the following: *Acetobacter aurantius, Acinetobacter baumannii, Actinomyces israelii, Agrobacterium radiobacter, Agrobacterium tumefaciens, Anaplasma, Anaplasma phagocytophilum, Azorhizobium caulinodans, Azotobacter vinelandii, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacteroides fragilis, Bacteroides gingivalis, Bacteroides melaninogenicus* (aka *Prevotella melaninogenica*), *Bartonella henselae, Bartonella quintana, Bordetella, Bordetella bronchiseptica, Bordetella pertussis, Borrelia burgdorferi, Brucella, Brucella abortus, Brucella melitensis, Brucella suis, Burkholderia, Burkholderia mallei, Burkholderia pseudomallei, Burkholderia cepacia, Calymmatobacterium granulomatis, Campylobacter, Campylobacter coli, Campylobacter fetus, Campylobacter jejuni, Campylobacter pylori, Chlamydia, Chlamydia trachomatis, Chlamydophila, Chlamydophila pneumoniae* (aka *Chlamydia pneumoniae*), *Chlamydophila psittaci* (aka *Chlamydia psittaci*), *Clostridium, Clostridium botulinum, Clostridium difficile, Clostridium perfringens* (aka *Clostridium* welchii), *Clostridium tetani, Corynebacterium, Corynebacterium diphtheria, Corynebacterium fusiforme, Coxiella* bumetii, *Ehrlichia chaffeensis, Enterobacter cloacae, Enterococcus, Enterococcus avium, Enterococcus durans, Enterococcus faecalis, Enterococcus faecium, Enterococcus galllinarum, Enterococcus maloratus, Escherichia coli, Francisella tularensis, Fusobacterium nucleatum, Gardnerella vaginalis, Haemophilus, Haemophilus ducreyi, Haemophilus influenza, Haemophilus parainfluenzae, Haemophilus pertussis, Haemophilus vaginalis, Helicobacter pylori, Klebsiella pneumonia, Lactobacillus, Lactobacillus acidophilus, Lactobacillus bulgaricus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium, Mycobacterium avium, Mycobacterium bovis, Mycobacterium diphtheria, Mycobacterium intracellulare, Mycobacterium leprae, Mycobacterium lepraemurium, Mycobacterium phlei, Mycobacterium smegmatis, Mycobacterium tuberculosis, Mycoplasma, Mycoplasma fermentans, Mycoplasma genitalium, Mycoplasma hominis, Mycoplasma penetrans, Mycoplasma pneumonia, Neisseria, Neisseria gonorrhoeae, Neisseria meningitides, Pasteurella, Pasteurella multocida, Pasteurella tularensis, Peptostreptococcus, Porphyromonas gingivalis, Prevotella melaninogenica* (aka *Bacteroides*

*melaninogenicus), Pseudomonas aeruginosa, Rhizobium radiobacter, Rickettsia, Rickettsia prowazekii, Rickettsia psittaci, Rickettsia Quintana, Rickettsia rickettsii, Rickettsia trachomae, Rochalimaea, Rochalimaea henselae, Rochalimaea Quintana, Rothia dentocariosa, Salmonella, Salmonella enteritidis, Salmonella typhi, Salmonella typhimurium, Serratia marcescens, Shigella dysenteriae, Staphylococcus, Staphylococcus aureus, Staphylococcus epidermidis, Stenotrophomonas maltophilia, Streptococcus, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumonia, Streptococcus pyogenes, Streptococcus rattus, Streptococcus salivarius, Streptococcus sanguis, Streptococcus sobrinus, Treponema, Treponema pallidum, Treponema denticola, Vibrio, Vibrio cholera, Vibrio comma, Vibrio parahaemolyticus, Vibrio vulnificus, Wolbachia, Yersinia, Yersinia enterocolitica, Yersinia pestis,* and *Yersinia pseudotuberculosis.*

Non-limiting examples of blood borne parasites that may be eradicated using the methods and the systems of the invention include *Plasmodium, Trypanosoma cruzi, Babesia microti,* and *Leishmania.*

Such pathogens may be present in the blood stream of the subject as a result of a natural transmission such as between humans, between animals or across species, as well as a result of contamination or a deliberate biological agent attack.

Importantly, just some reduction in the count of such pathogens and not its complete eradication may already be clinically useful in allowing the subject more time to upregulate its natural defenses. The blood treatment of the subject may be conducted once or repeated from time to time, such as every 10 min, 30 min, 1 hour, 2 hours, 3 hours, 6 hours, 12 hours, 24 hours, 48 hours, 72 hours, 96 hours, weekly, bi-weekly, monthly or on any other schedule prescribed by a physician.

In addition to reducing pathogens, UV irradiation of blood may be conducted for a number of other therapeutic purposes, such as the following:

Energize or enhance the natural biochemical and physiological defenses of the body by introducing of ultraviolet energy into the blood stream. UV irradiation may not kill every pathogen in the body directly. Rather UV exposure transmits energy to the blood that empowers a strong biochemical response thereto, including stabilization of white blood cells, and increasing cell membrane permeability (which may enhance the body's ability to produce antibodies) Furthermore, the debris from dead pathogens may stimulate the immune response further against even the most stubborn pathogens;

Rapidly detoxify and relieve toxemia;

Increase venous blood oxygen in subjects with depressed blood oxygen values. Oxygen in the blood has a powerful effect, helping to eradicate not only pathogens, but it also creates an environment in which yeasts, fungi, and cancer cells cannot exist;

Reduce edema (swelling and water retention outside of the cells);

Stimulate red blood cell production;

Control nausea and vomiting.

In embodiments, UV irradiation of blood may be used as treatment for a number of ailments including Inflammatory conditions (for example Acute thrombophlebitis, Fibrositis, Bursitis, Nephritis, Iritis, uveitis, Cholecystitis, Pancreatitis, Rheumatoid arthritis), Circulatory conditions (for example Varicose and diabetic ulcers, Peripheral vascular disease, Gangrene, Vascular headaches), and other conditions (for example Non-healing Wounds and Fractures, Pemphigus, Emphysema, Adjunctive cancer treatment).

According to the invention, blood from a subject may be withdrawn using a traditional venous or arterial catheter and directed towards the system of the invention. After treatment, blood may be returned to the subject. In some embodiments, removal, treatment and return of blood may be conducted at the same time. In other embodiments, a predetermined volume of blood may be withdrawn, treated and then returned to the subject, such volume may be 20 cc, 30 cc, 50 cc, 75 cc, 100 cc, 150 cc, 200 cc, 250 cc, 300 cc, 400 cc, 500 cc, 600 cc, 750 cc or any other volume therebetween.

While in the system, blood may be subjected to at least the following two steps:

(a) Exposure to sufficient levels of UV irradiation in order to reduce pathogens therein—such as at a peak wavelength from about 250 nm to about 270 nm. Such exposure may be accomplished by propagating the blood along a flow path in a vicinity of a suitable source of UV-irradiation using a suitable blood pump; and (b) Exposure to UV light may be achieved while minimizing heat transfer to the blood by the source of UV irradiation—by separating the blood from UV source using a layer of IR-absorbing fluid.

The details of separating blood from UV source by a layer of IR-absorbing fluid to prevent the unwanted IR irradiation from reaching the biological fluid are described below. The method may further include active cooling of blood to maintain its temperature within a desirable temperature range, which may be selected to prevent its degradation and thermal damage to any of its components.

Other elements and components may be included in the circuit for treating blood such as additional or intermediate storage bags, gas bubble traps, various sensors such as fluid pressure, UV intensity monitor/sensor, flow, and temperature sensors, additional blood pumping devices, filters, etc.

Figure 2:
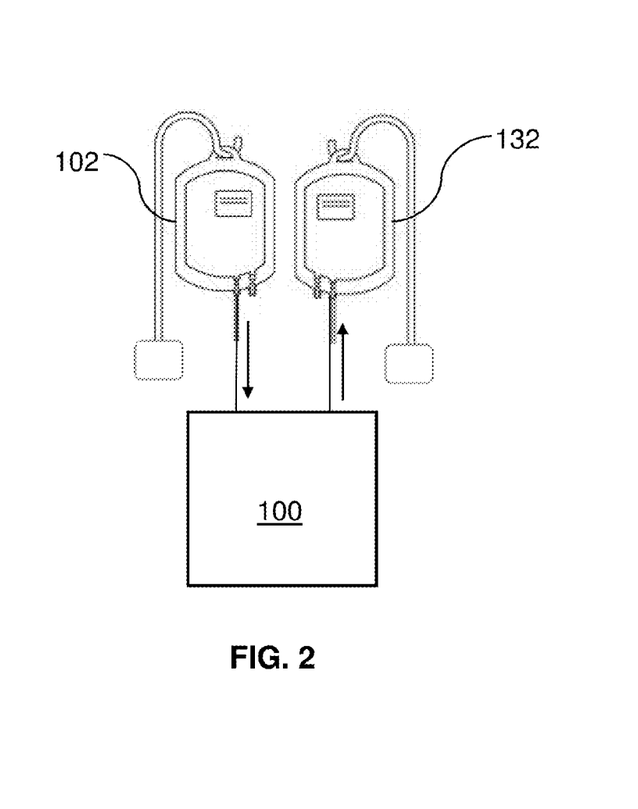
FIG. 2 is a general schematic view of the system of the invention used to treat a unit of collected donor blood.

The same or similar system may also be used for treating donor blood before its subsequent separation into various components and/or storage for use with another subject in the future. The requirements for pathogen reduction are much higher in this case but the general concept remains the same. FIG. 2 shows one example of how blood (such as freshly collected donor blood) contained in the storage bag 102 may be withdrawn into the system 100 of the present invention, treated to expose the blood to UV irradiation and then placed into another bag 132 for subsequent processing, separation into components, immediate use for another subject and/or storage.

Figure 3:
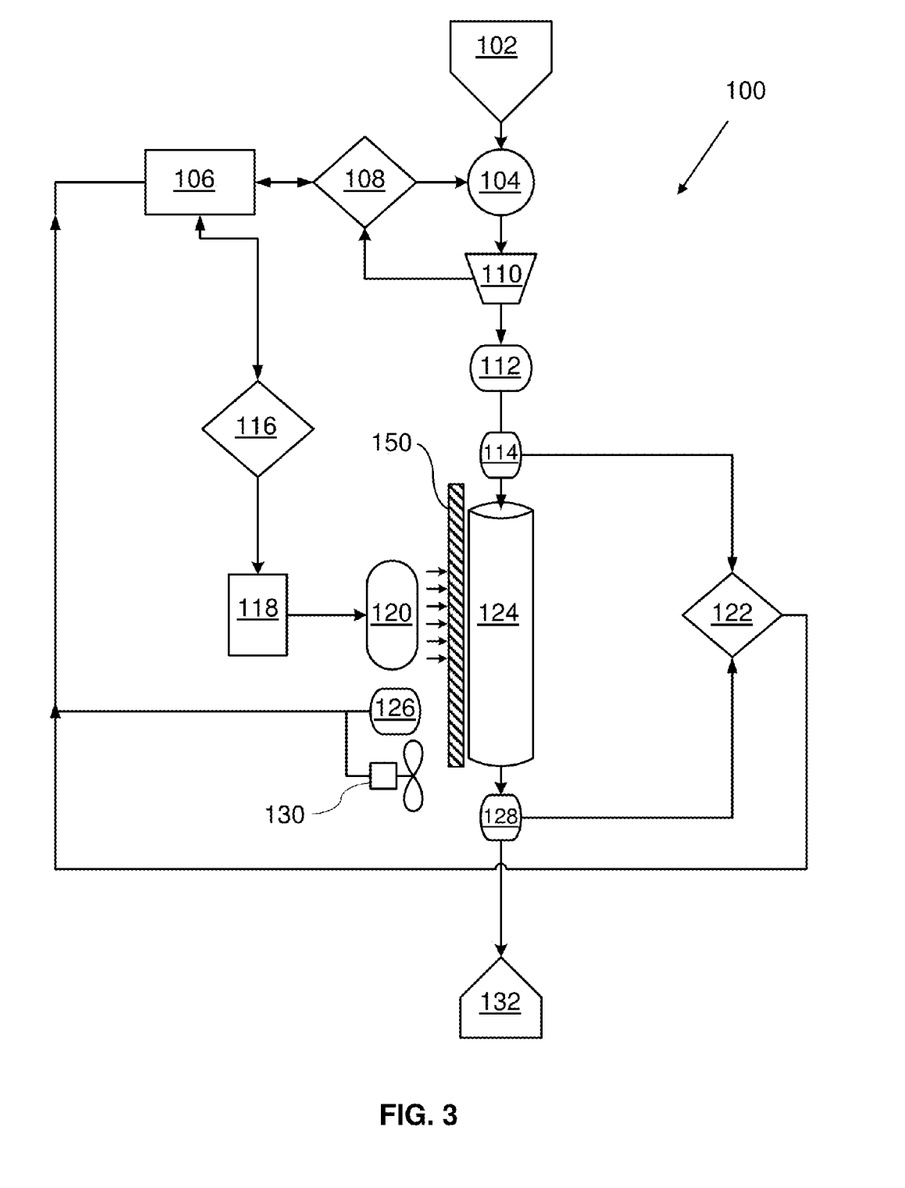
FIG. 3 is a general schematic view of the components of the system of the invention.

FIG. 3 shows a general block-diagram of the system 100 of the invention. A fluid supply source 102 may be used to draw the biological fluid from. As mentioned above, such fluid supply source may be a unit of blood collected from a donor, for example. Biological fluid may be drawn from or gravity-fed into a pump 104 suitable for the purposes of pumping the biological fluid. A variety of pumps may be used for the purposes of the present invention. In the case of processing blood or blood products, a biocompatible atraumatic pump may be used such as a suitable peristaltic pump, centrifugal pump, diaphragm pump or another blood-compatible pump. The pump 104 may be controlled by a pump controller 108, which in turn may be operable by a central control unit 106, which in turn may be driven by a microprocessor to automate at least some or most operations of the system 100. The pump controller 108 may be operated to cause the pump 104 to propagate the biological fluid through the exposure chamber of the system 100 with a desired constant or variable rate. The central control unit 106 may be further equipped with computer memory to store the preferred modes of operation, accumulate usage data, record alert conditions, etc.

Figure 4:
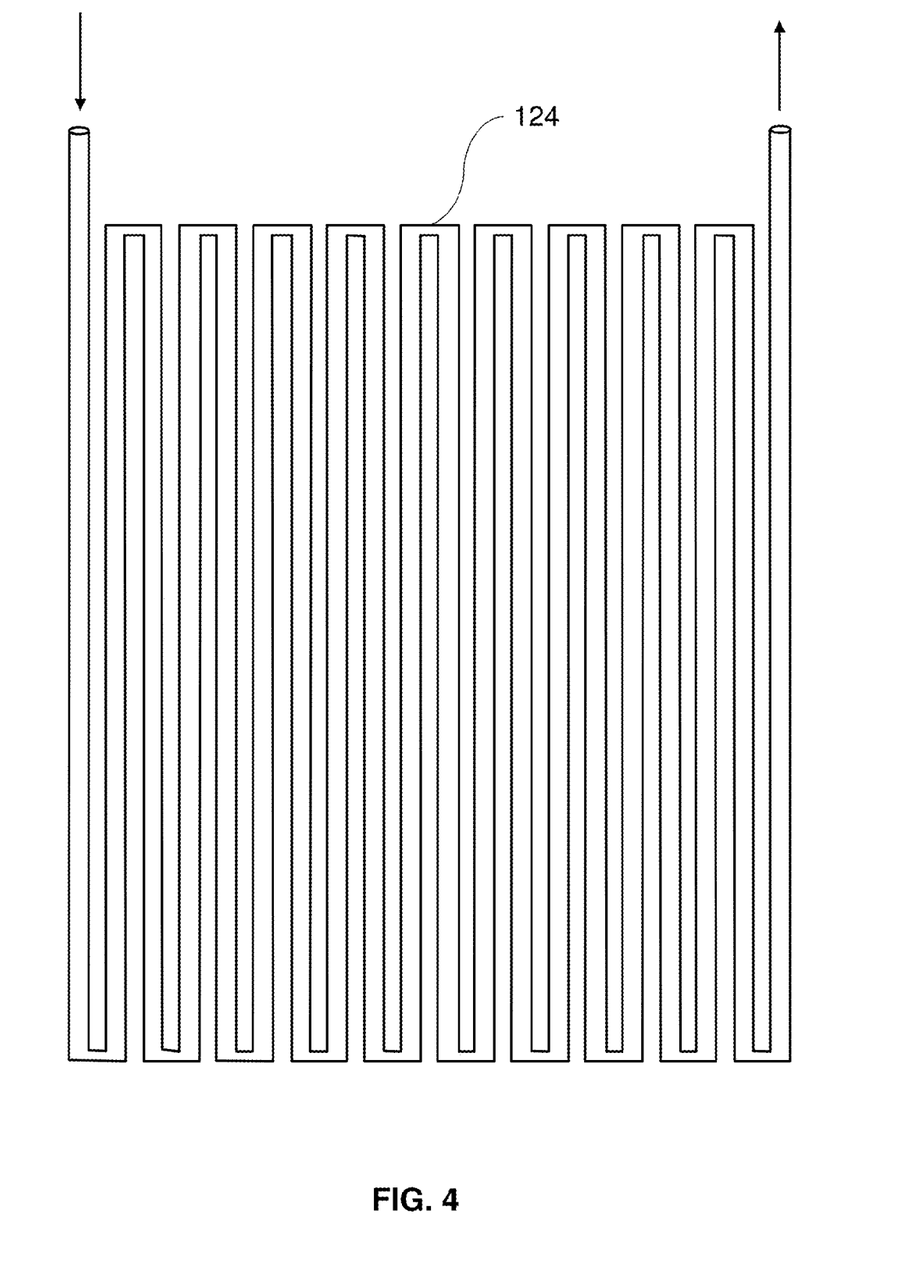
FIG. 4 shows a serpentine flow path.
Figure 5:
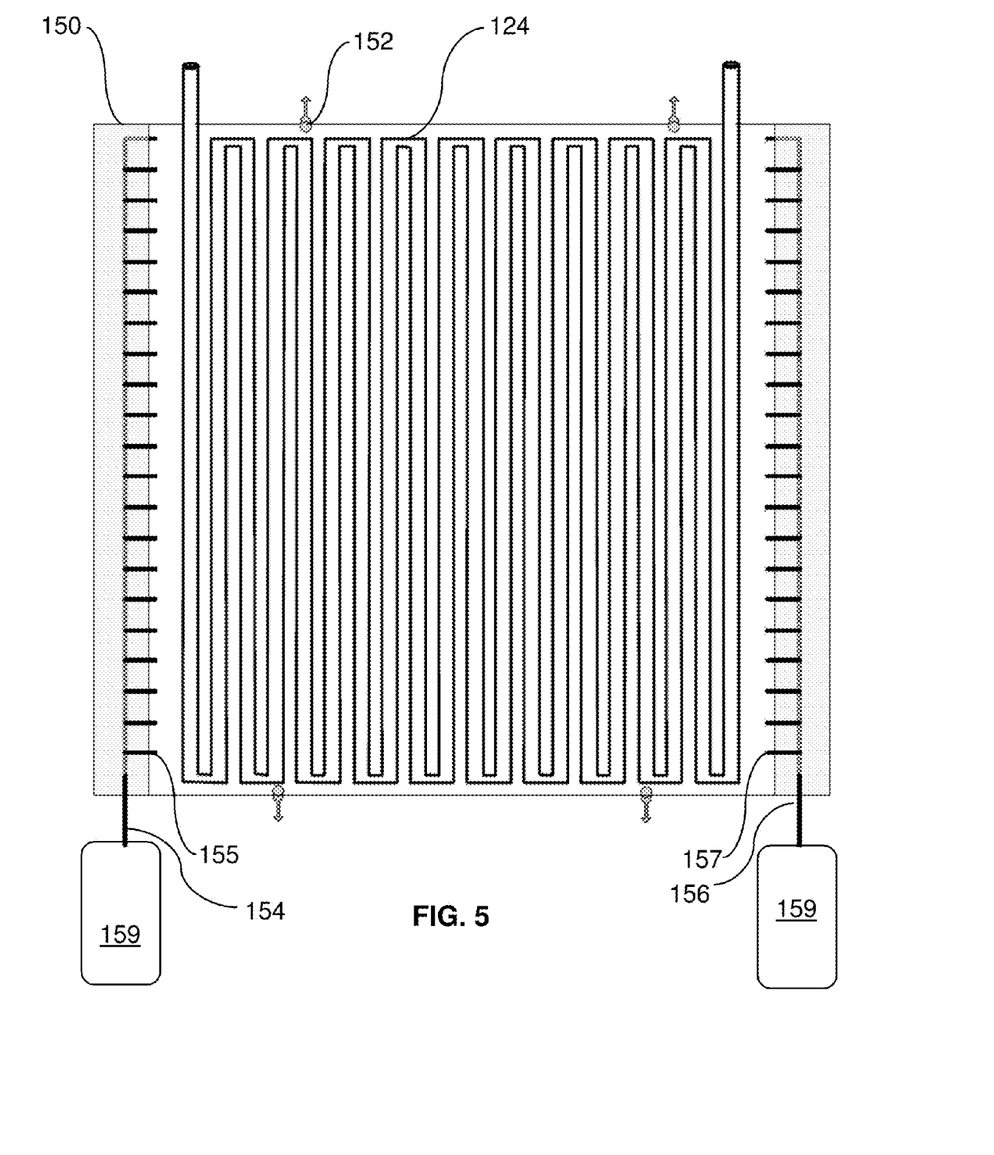
FIG. 5 shows one embodiment of the jacket containing IR-absorbing fluid surrounding the serpentine flow path of the system in which the direction of IR-absorbing fluid propagating through the jacket is perpendicular to the direction of biological fluid propagating through the serpentine flow path.
Figure 6:
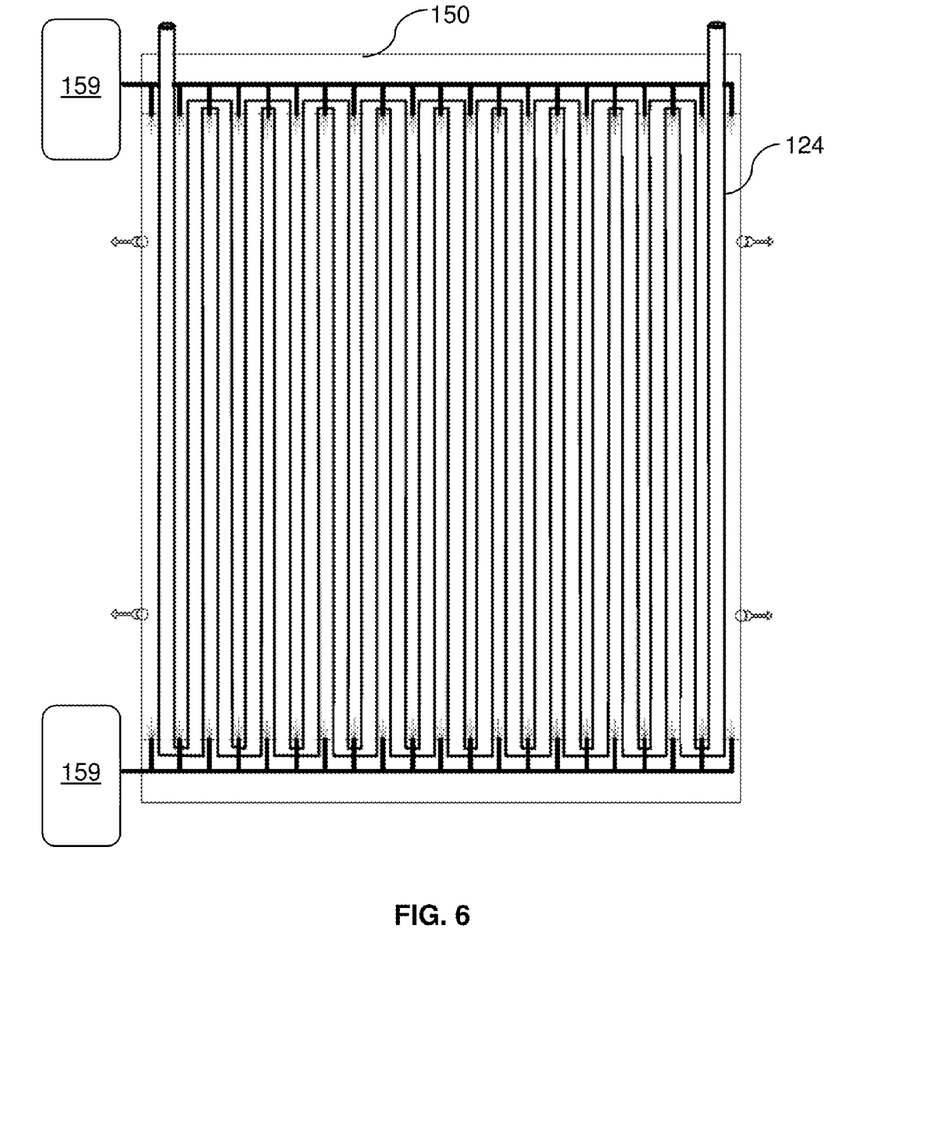
FIG. 6 shows another embodiment of the jacket containing IR-absorbing fluid in which the direction of IR-absorbing fluid propagating through the jacket is parallel to the direction of biological fluid propagating through the serpentine flow path.
Figure 7:
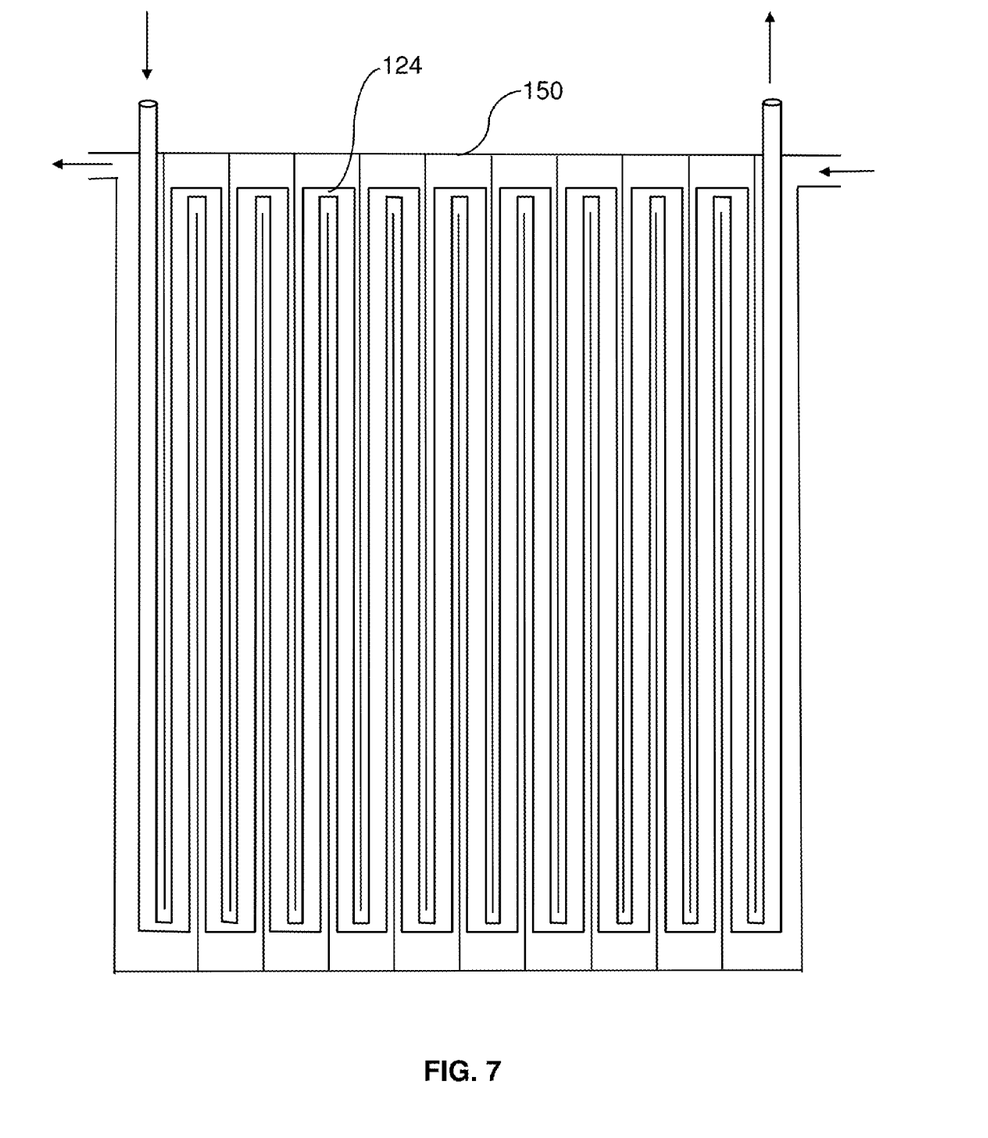
FIG. 7 shows yet another embodiment of the jacket which surrounds the flow path and in which the direction of IR-absorbing fluid propagating therethrough is opposite to the direction of biological fluid propagating through the serpentine flow path.

The biological fluid may be pumped by the pump 104 from the fluid supply 102 through the optional flow sensor 110 (operably connected to the pump controller 108), and further through an optional inlet pressure sensor 112 and an optional inlet temperature sensor 114 prior to entering the exposure chamber, which includes a fluid flow path 124 described in greater detail below with reference to FIG. 4.

A source of UV irradiation 120 may be used to provide UV irradiation suitable for reducing pathogens in the biological fluid while in the exposure chamber. A plurality of UV irradiation lamps or lights may form together the combined source of UV irradiation 120. Utilizing such plurality of lamps or lights as opposed to a single lamp or light allows a more uniform UV exposure over a greater portion or preferably the entire fluid flow path 124. The UV irradiation source 120 may be operated by a UV light source driver 118, which in turn may be controlled by the UV source control circuit 116 operable by the central control unit 106. As described in further details below, a layer of IR-absorbing fluid 150 may be placed between the source of UV irradiation 120 and the flow path 124 to preclude or at least reduce exposure of the flow path to IR irradiation.

Following the exit from the flow path 124, the biological fluid may be directed through an optional outlet temperature sensor 128 towards the outlet fluid collection element 132, such as a blood collection bag for example.

Additional elements of the system 100 may include a biological fluid temperature control system 122, which may be operably connected to the inlet temperature sensor 114 and the outlet temperature sensor 128 to detect a potential increase in fluid temperature above a predetermined safe threshold. Such temperature increase may be caused by too much energy passed into the biological fluid from the source of UV irradiation 120, deliberate decrease of pump flow or by an inadvertent slow-down of the pump 104 causing an increase in residence time of the biological fluid while inside the flow path 124. In any case, the optional fluid temperature control system 122 may be connected to the central control unit 106 and used to at least trigger an alarm. In some embodiments, the system 122 may be used to activate or regulate (increase or decrease) the active cooling of the flow path 124 and the biological fluid contained therein so as to maintain its temperature within allowable safe limits.

The cooling of the UV irradiation source 120 and/or the flow path 124 may be accomplished in a number of known ways. Passive cooling may be accomplished by using a heat sink or by providing passive vents to expose the outer surfaces of the flow path to atmosphere. Active air cooling may be accomplished by providing one or more fans 130 or other cooling devices such as Peltier coolers thermally coupled to the heat sink, wherein such cooling devices may be activated upon either the biological fluid or a source of UV irradiation 120 reaching an upper limit of their respectfully allowable safe temperatures. Liquid cooling systems may also be provided as an alternative to air cooling. Such liquid cooling systems may include circulation of a cooling liquid in thermal contact with the source of UV irradiation 120 and/or the fluid flow path 124. When pumping blood or blood products, the safe upper temperature limit for the biological fluid may be set at 42 degrees C. For UVC irradiating LEDs, the upper safe temperature limit may selected to be about 50 degrees C. (ideal operating temperature may be about room temperature, or 20 to 25 degrees C. while the maximum allowable temperature may not be above 100 degrees C.—higher operating temperature caused a significant reduction in UV output).

In embodiments, the cooling elements of the system (such as cooling fans 130) may be activated for the entire duration of UV irradiating the biological fluid or for a portion thereof. The cooling elements may be activated on a predefined intermittent schedule or based on the feedback from the temperature sensors 114 and 128 or the optional temperature sensors 126 configured to detect the temperature of the source of UV irradiation 120.

In further embodiments, the layer of IR-absorbing fluid may by itself be used to both absorb the undesirable IR irradiation and cool the biological fluid while in the exposure chamber—as described in greater detail below.

FIG. 4 shows a side view of the flow path 124, which may be selected to be sufficiently long to provide for sufficient UV exposure for the biological fluid propagating therethrough. The length of the flow path may vary from about 0.1 meter to about 20 meters. In embodiments, the length of the flow path may depend on the diameter thereof, the rate of biological fluid flow, the intensity of UV irradiation, the desired efficacy of pathogen reduction ("log kill" limit) and other factors. In various embodiments, the length of the flow path 124 may be selected to be from about 4 meters to about 20 meters. In embodiments, the length of the flow path may be selected to be about 4 meters, about 6 meters, about 8 meters, about 10 meters, about 12 meters, about 14 meters, about 16 meters, about 18 meters, about 20 meters or any length in-between these numbers.

The cross-sectional shape of the flow path 124 may be selected to be flat, oval, or round. The flat shape may be selected to have a wide portion thereof to be exposed to the source of UV irradiation 124 so as to maximize the exposure of the biological fluid to UV light.

In case of a round cross-sectional shape, the internal diameter of the flow path 124 may be selected to be from about 1 mm to about 15 mm. In embodiments, the internal diameter of the flow path 124 may be selected to be about 1 mm, about 2 mm, about 3 mm, about 4 mm, about 5 mm, about 6 mm, about 7 mm, about 8 mm, about 10 mm, about 12 mm, about 15 mm or any diameter in-between these numbers.

To provide a substantial length of the flow path in a small package, various methods of folding the flow path 124 into a compact structure may be used. One such method is to form the flow path in a serpentine shape as shown in FIG. 4 with a well-defined inlet and outlet indicated by arrows in FIG. 4. The serpentine-shaped flow path 124 may be formed along a single flat plane so as to allow its exposure on both sides to the sources of UV irradiation 120 as described below. Alternatively, the serpentine shape may be wrapped about a centrally-placed source of UV irradiation 120 or otherwise presented in a compact way to make the entire system easy to use and transport.

In embodiments, all or some elements of the system 100 which are in direct contact with the biological fluid may be made disposable or reusable. In some embodiments, only the flow path 124 may be made disposable. In other embodiments, the flow path 124 along with the tubing for the peristaltic pump 104 as well as the necessary sensors or sensor access points may all be formed as a disposable cassette or a cartridge for easy handling before, during and after use. Such disposable cassette may have provisions to "plug into" the rest of the system including reusable UV irradiation source 120, the active portion (rollers) of the pump 104, and all the elements of the above described control system. Once assembled, the disposable portion of the system 100 may be attached at the inlet to the source 102 of biological fluid and at the outlet to the fluid collection element 132.

The serpentine-shaped flow path 124 may be made from a UV-transparent material such as glass, and in particular quartz glass. Alternatively, the flow path may be formed from plastics such as organic polymers, co-polymers and the like such as but not limited to cellulose products, PTFE, FEP, PVC and PE. In general, these materials have UV transmission properties in the range from 30 to 95% for a typical wall thickness, which may generally be between about 0.3 mm and about 4 mm.

Helical flow mixers may be installed along a portion or the entire length of the flow path 124. Such mixers may be used to cause propagating biological fluid to undergo intense mixing so as to expose all elements thereof to the outside surface and subsequently to UV irradiation.

Figure 8:
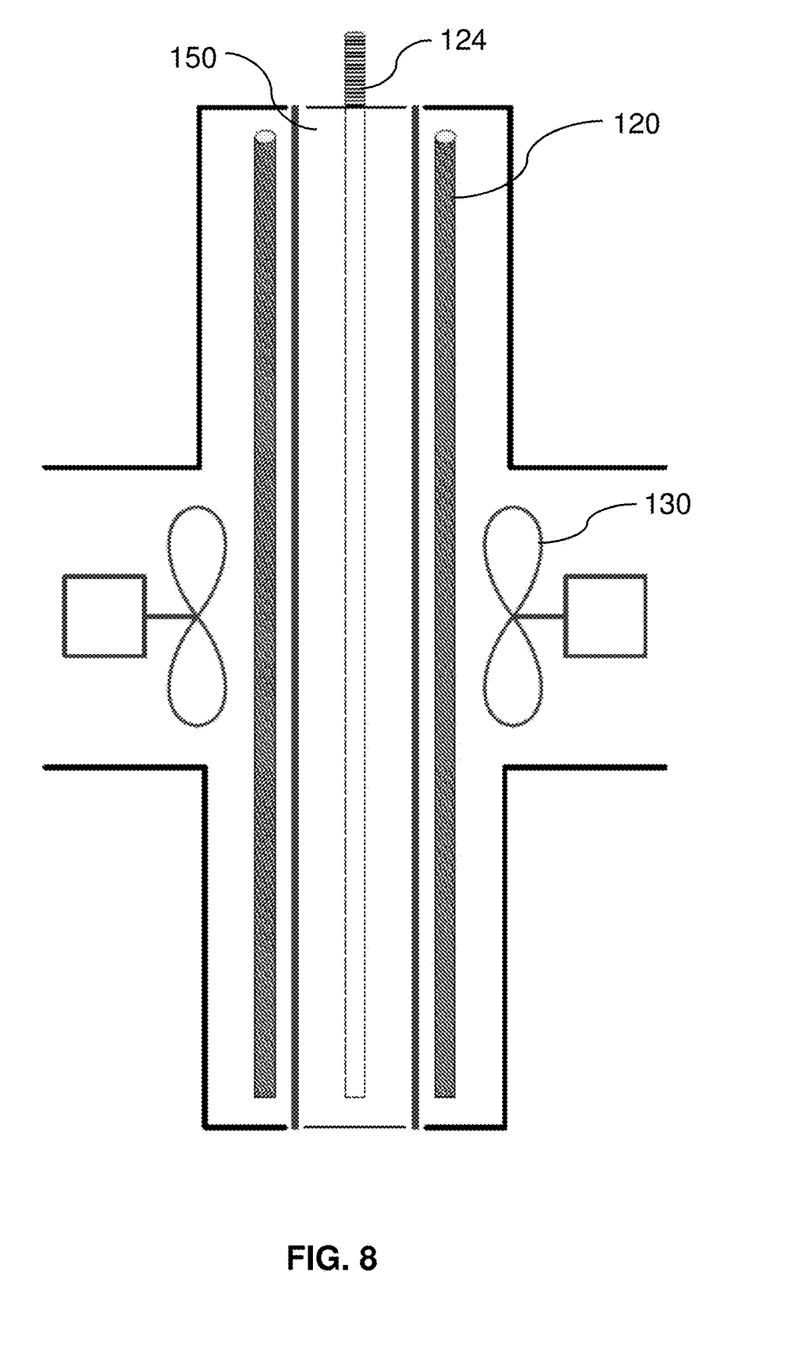
FIG. 8 is a side view of the key elements of the system of the invention.
Figure 9:
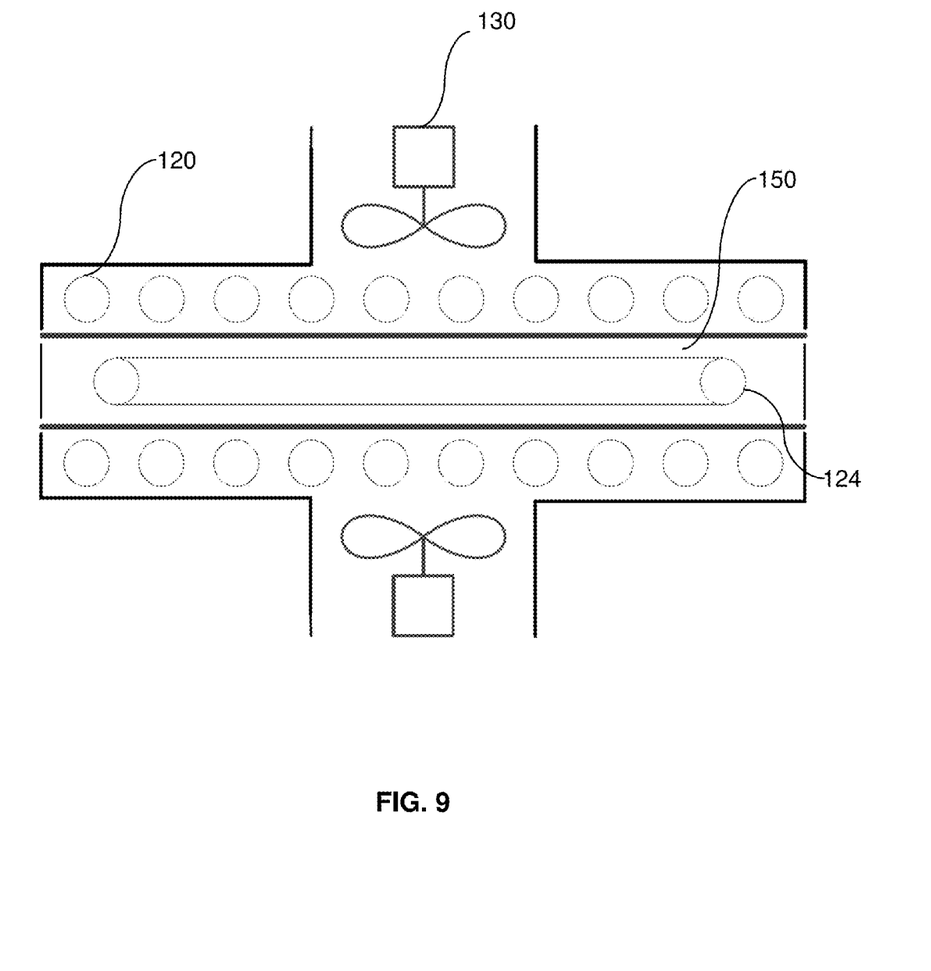
FIG. 9 is a top view of the same.

To prevent the IR irradiation from reaching the biological fluid during UV exposure, the present invention uses a layer of IR-absorbing fluid positioned between the source of UV irradiation 120 and the flow path 124 containing the biological fluid. The layer design and the choice of the fluid may be made to assure at least substantial or preferably complete passing of the UV light therethrough in the desired therapeutic range such as UVC light. At the same time, the IR-absorbing fluid may be selected to absorb at least 50% or preferably the entire light energy in the IR wavelength spectra so as to prevent it from reaching the biological fluid. Non-limiting examples of such IR-absorbing fluid include various liquids and gases such as carbon dioxide, water vapor, methane, nitrous oxide, and ozone. Carbone dioxide may be particularly useful as it is readily available, safe, and can be harmlessly discharged into atmosphere in small quantities needed for the purposes of the present invention.

FIG. 5 shows an example of the flow path 124 surrounded by a UV-transparent jacket 150 containing an IR-absorbing fluid, such as carbon dioxide. The jacket may completely surround the flow path 124 to place the IR-absorbing fluid in close thermal contact with the exterior of the flow path 124 as seen in FIG. 5 or may be placed to separate the flow path 124 from the source of UV irradiation 120 on one side thereof.

The UV-transparent jacket 150 may be made from the same material as the flow path 124, such as glass, and in particular quartz glass. Alternatively, the jacket 150 may be formed from plastics such as organic polymers, co-polymers and the like, for example cellulose products, PTFE, FEP, PVC and PE.

The thickness of the layer of IR-absorbing fluid may be selected to absorb at least a substantial portion of IR irradiation, such as over 50% thereof or greater. Depending on the choice of the UV irradiation source 120 and the choice of the IR-absorbing fluid, the thickness of its layer may be selected to be anywhere from about ¼ of an inch to 3 inches. In embodiments, the thickness of the IR-absorbing fluid may be about ¼ of an inch, about ½ of an inch, about ¾ of an inch, about 1 inch, about 1.5 inches, about 2 inches, about 2.5 inches, about 3 inches or any suitable thickness inbetween.

Shown in FIG. 5 is a left manifold 154 with a plurality of nozzles 155 and a right manifold 156 with a plurality of nozzles 157. Either one or both manifolds may be used to inject the IR-absorbing fluid into the jacket 150 so as to envelope the flow path 124 and separate thereof from the source of UV irradiation 120. One or more pressure relief valves 152 may also be included to be a part of the jacket. In embodiments, the IR-absorbing fluid may be introduced through one of the manifolds 154 or 156 so it passes through the jacket 150 in a direction perpendicular to that of the flow of the biological fluid through the flow path 124—in the design shown in FIG. 5, IR-absorbing fluid flows laterally while the biological fluid is propagated vertically. After passing over the biological fluid, the IR-absorbing fluid may be collected using the opposite manifold 156 or 154. After collecting, the IR-absorbing fluid may be reintroduced on the opposite side of the jacket 150 and reused. In some embodiments, the IR-absorbing fluid may be cooled or otherwise conditioned after each passage over the fluid flow path 124. Active circulation of the IR-absorbing fluid over the flow path 124 may be used to accomplish two purposes: absorb IR irradiation and cool the flow path 124. In that case, the temperature of the IR-absorbing fluid introduced into the jacket 150 may be selected to be below that of the biological fluid inside the flow path 124.

Alternatively, the IR-absorbing fluid may be injected into the jacket 150 and kept in a static state under constant pressure for the duration of the procedure. In embodiments, the IR-absorbing fluid may be pressurized so as to increase its density. This may be particularly advantageous in the case of a gas used for such purpose, in particular using carbon dioxide. Such IR-absorbing gas may be pressurized to be above atmospheric pressure by about 1 ATM, about 10 ATM, about 20 ATM, about 30 ATM, about 50 ATM, about 75 ATM, about 100 ATM, about 150 ATM or any suitable pressure inbetween.

In further embodiments, the pressurized IR-absorbing fluid such as compressed carbon dioxide may be introduced into the jacket 150 from one or more pressurized canisters 159 through one or both manifolds 154 and 156 and allowed to be vented to atmosphere through the relief valves 152 during the procedure. Canisters 159 may contain the IR-absorbing gas at high pressures that may exceed 100 ATM. The opening level of pressure relief for the valves 152 may be selected to be below the pressure of gas introduced into the jacket 150 and may range from atmospheric pressure to any pressure listed above up to about 150 ATM. One advantage of this approach is a natural cooling effect occurring once the pressurized gas enters a lower pressure environment of the jacket 150. Reduction of gas pressure leads to a drop of its temperature, which may by itself be sufficient to cool the flow path 124 and maintain the temperature of the biological fluid therein at safe levels.

In embodiments, the flow of IR-absorbing fluid may be arranged to be in a direction other than that of the biological fluid circulating in the flow path 124. FIG. 5 shows an example when the direction of the IR-absorbing fluid is perpendicular to the direction of the biological fluid. FIG. 6 shows a configuration of the system in which the direction of flow of the IR-absorbing fluid is along the direction of flow of the biological fluid along some portions of the flow path 124 and opposite in some other portions of the flow path 124. FIG. 7 shows yet another configuration of the system in which the serpentine-shaped flow path 124 is enclosed in a respectively larger size serpentine-shaped channel for IR-absorbing fluid. The direction of flow of both fluids may be selected to be opposite to each other so as to maximize the heat exchange therebetween.

FIG. 8 shows a side view of one embodiment of the system in which the flow path 124 is separated from sources of UV irradiation 120 located on both sides thereof by a layer of IR-absorbing fluid 150. FIG. 9 shows a top view of the same showing a plurality of spaced apart UV lights 120 located on both sides of the flow path 124.

Figure 10:
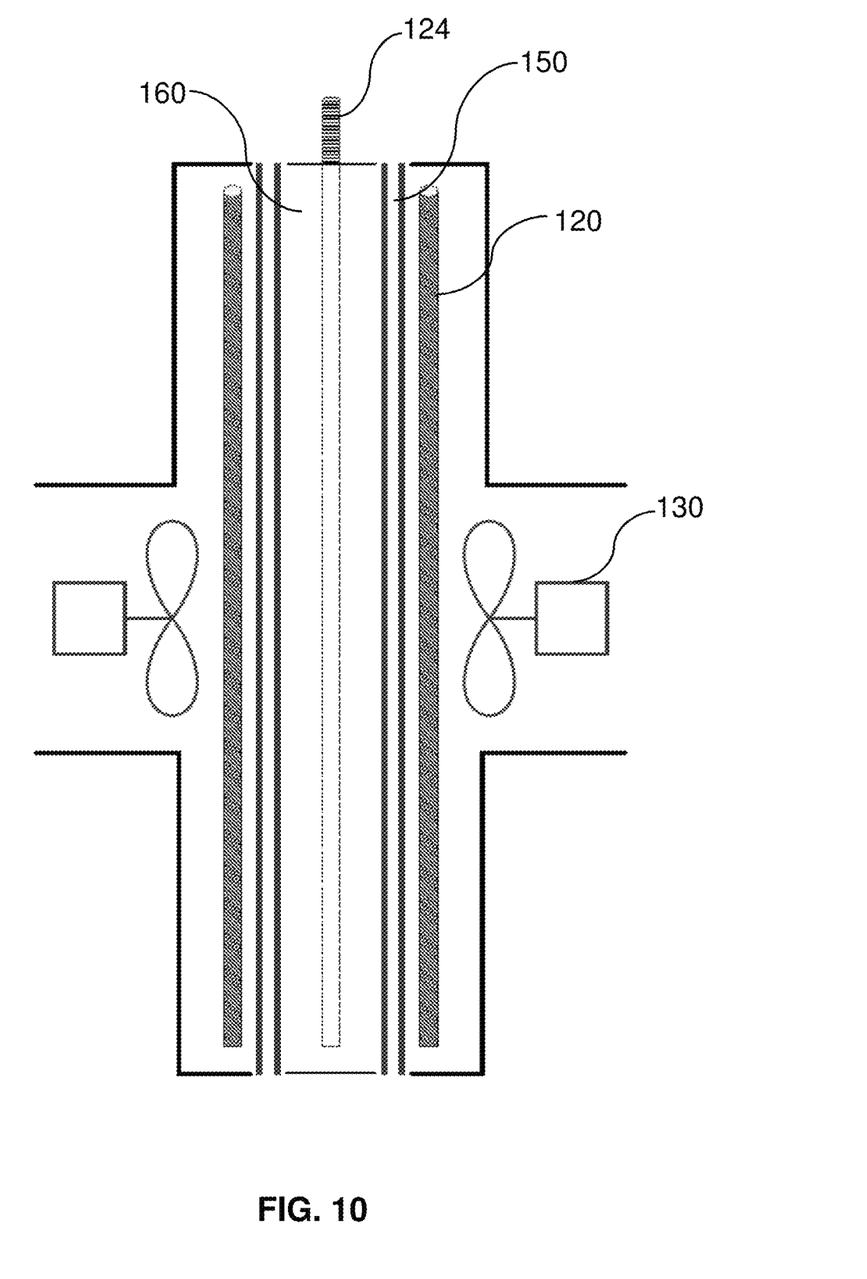
FIG. 10 is a side view of an alternate configuration of the system of the invention.

FIG. 10 shows yet another alternative arrangement in which the action of absorbing IR is separated from the action of cooling the biological fluid. To accomplish these objectives separately, a layer of cooling fluid or gas 160 may be positioned in close thermal contact with the exterior of the flow path 124 which the layer of IR-absorbing fluid 150 may be positioned outside the cooling layer 160 but still between the flow path 124 and the source of UV irradiation 120 so as to preclude the IR portion of light irradiation emanating from the source 120 from reaching the biological fluid inside the flow path 124. The cooling fluid may be circulated using the system 122 as described in greater detail above.

In use, the system of the invention may be operated in the following way. Initial supply of the biological fluid may be positioned in the fluid supply source 102. The entire fluid-contacting circuit as described above may be primed or filled with inert gas, carbon dioxide, saline or the biological fluid itself may be pumped therethrough by the pump 104. The processing of the biological fluid may then be initiated by activating the source of UV irradiation 120 and the pump 104.

Pumping of the biological fluid through a serpentine-shaped flow path 124 causes it to be exposed to UV irradiation. Active mixing of the fluid is designed to bring pathogens to the surface of the flow and inactivate them by UV light. Flow mixing may be achieved by varying the flow through the pump 104 or by using static mixers in the flow path 124.

While in the flow path 124, the biological fluid may be protected from overheating by the layer of IR-absorbing fluid as described above.

EXPERIMENTS AND EXAMPLES

Figure 11:
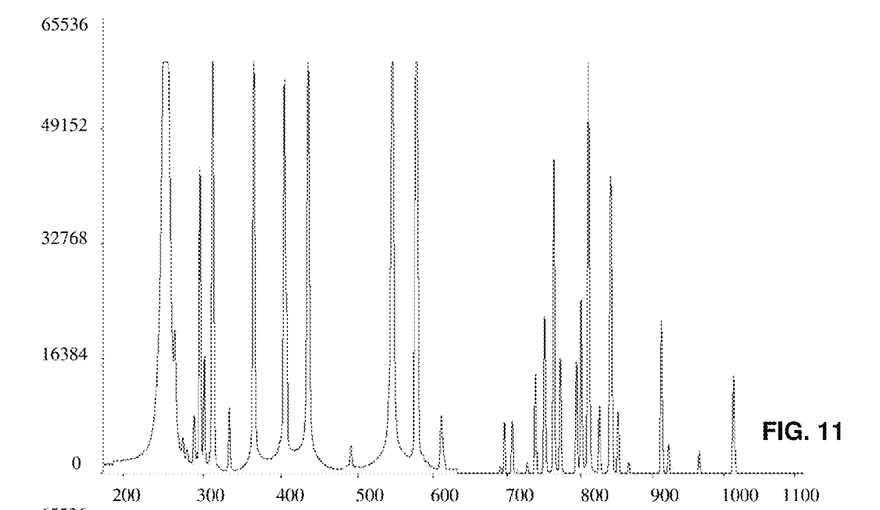
FIG. 11 is a graph showing various wavelengths of the UV lamp output prior to utilization of the IR-absorbent layer.
Figure 12:
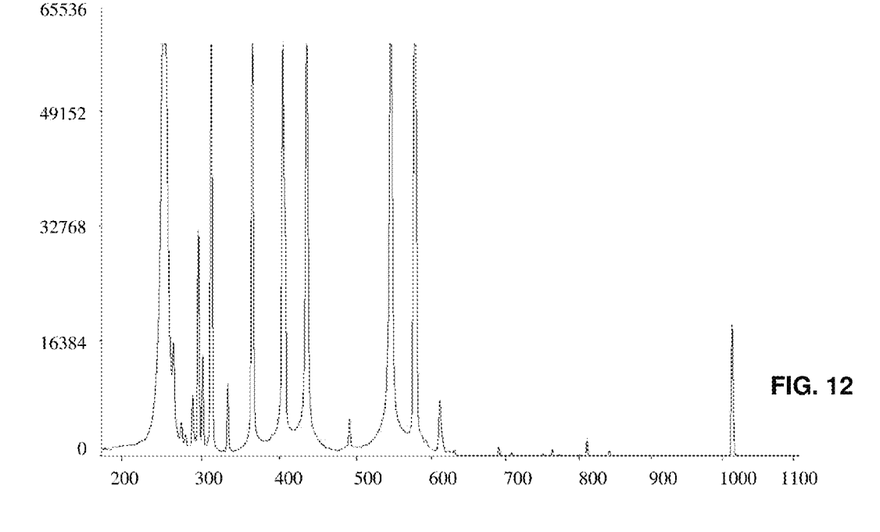
FIG. 12 is a graph showing remaining wavelengths after passing the output of a UV lamp through a layer of an IR-absorbing fluid.

A series of tests has been conducted starting in spring of 2010 to analyze the spectra of wavelength emanating from various sources of UV irradiation. FIG. 11 shows a typical example of spectra coming out of a UV lamp. As seen in the figure, a broad range of wavelengths are emanated by the lamp including a strong IR presence in the range over 700 nm. As described earlier, the desired wavelength range for the purposes of reducing pathogens is quite narrow—from about 250 nm to about 270 nm. All other wavelengths cause heating of the biological fluid when absorbed by it and in that sense are believed to be undesirable.

Use of a layer of IR-absorbing fluid (in this case $CO_2$) was evaluated for the purposes of shielding the biological fluid from the IR portion of the spectra. FIG. 12 shows an exemplary spectra of the same UV lamp after passing through a layer of $CO_2$. As can be seen, almost the entire portion of the IR spectra is no longer visible in FIG. 12, indicating that the biological fluid is no longer exposed thereto.

The herein described subject matter sometimes illustrates different components or elements contained within, or connected with, different other components or elements. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for treating blood comprising a step of propagating said blood through an elongated flow path while irradiating thereof with ultraviolet light through a layer of IR-absorbing fluid, said IR-absorbing fluid being gas or water vapor pressurized by at least 1 atmosphere above atmospheric pressure.

2. The method as in claim 1 further comprising the following steps:

a. exposing said blood to UV irradiation at a peak wavelength from about 250 nm to about 270 nm, and b. minimizing heat transfer to said blood from a source of UV irradiation by separating said blood therefrom using a layer of IR-absorbing fluid.

3. The method as in claim 2 further comprising a step of cooling said blood so as to maintain the temperature thereof within a predetermined range.

4. The method as in claim 2 further comprising a step of removing blood from a subject prior to step (a) and a step of returning said blood after inactivation of pathogens therein to said subject.

5. The method as in claim 4, wherein said pathogen is contracted by said subject via a natural transmission, contamination, or as a result of a biological agent attack, said pathogen is selected from a group consisting of a virus, a bacteria, a fungi, and a parasite.

6. The method as in claim 2, wherein said blood is withdrawn from a donor prior to step (a), said blood is stored or processed after completion of step (b).

* * * * *